(12) United States Patent
Weimann

(10) Patent No.: US 7,232,431 B1
(45) Date of Patent: **\*Jun. 19, 2007**

(54) INTRADERMAL INCORPORATION OF MICROPARTICLES CONTAINING ENCAPSULATED DRUGS USING LOW FREQUENCY ULTRASOUND

(75) Inventor: Ludwig J. Weimann, Burlington, VT (US)

(73) Assignee: Ultra-Sonic Technologies, L.L.C., Georgia, VT (US)

( * ) Notice: Subject to any disclaimer, the term of this patent is extended or adjusted under 35 U.S.C. 154(b) by 674 days.

This patent is subject to a terminal disclaimer.

(21) Appl. No.: 10/672,032

(22) Filed: Sep. 26, 2003

Related U.S. Application Data

(63) Continuation-in-part of application No. 10/058,627, filed on Jan. 28, 2002, now Pat. No. 6,712,805.

(60) Provisional application No. 60/264,803, filed on Jan. 29, 2001.

(51) Int. Cl.
*A61M 31/00* (2006.01)

(52) U.S. Cl. .......................................... 604/500; 604/22

(58) Field of Classification Search .................. 604/19, 604/20, 500, 501, 22; 606/9
See application file for complete search history.

(56) References Cited

U.S. PATENT DOCUMENTS

| | | | |
|---|---|---|---|
| 4,691,724 A | 9/1987 | Garcia et al. | |
| 4,767,402 A | 8/1988 | Kost | |
| 4,844,882 A | 7/1989 | Widder et al. | |
| 5,016,615 A * | 5/1991 | Driller et al. | 601/2 |
| 5,384,133 A | 1/1995 | Boyes | |
| 5,421,816 A | 6/1995 | Lipkovker | |
| 5,688,233 A | 11/1997 | Hoffman | |
| 5,814,599 A | 9/1998 | Mitragotri | |
| 5,947,921 A | 9/1999 | Johnson | |
| 6,024,717 A | 2/2000 | Ball et al. | |
| 6,030,374 A | 2/2000 | McDaniel | |
| 6,143,276 A | 11/2000 | Unger | |
| 6,234,990 B1 | 5/2001 | Rowe et al. | |
| 6,322,532 B1 | 11/2001 | D'sa et al. | |
| 6,385,487 B1 | 5/2002 | Henley | |
| 6,416,740 B1 * | 7/2002 | Unger | 424/9.52 |
| 6,464,680 B1 | 10/2002 | Briskin et al. | |
| RE38,000 E | 2/2003 | Henley | |
| 6,712,805 B2 * | 3/2004 | Weimann | 604/500 |

\* cited by examiner

*Primary Examiner*—Nicholas D. Lucchesi
*Assistant Examiner*—Christopher D. Koharski
(74) *Attorney, Agent, or Firm*—Elman Technology Law, P.C.; Gerry J. Elman

(57) ABSTRACT

An apparatus for sonoporation for transdermal delivery of a microparticles suspension containing microencapsulated drugs includes a container containing said microparticles suspension and an ultrasound horn having a tip submerged in said microparticles suspension containing microencapsulated drug or the like. The ultrasound radiation is applied to generate cavitation bubbles, thus causing pores to be formed in the skin of a patient. The ultrasound radiation intensity and distance from the skin are also effective in generating ultrasonic jets driving the microparticles through the formed pores into the skin. The ultrasound radiation is desirably applied at a frequency other than a resonant frequency of the microparticles to avoid rupturing them.

25 Claims, 9 Drawing Sheets

INTRADERMAL INCORPORATION OF MICROPARTICLES CONTAINING ENCAPSULATED DRUGS USING LOW FREQUENCY ULTRASOUND

RELATED APPLICATION

This is a continuation-in-part of U.S. patent application Ser. No. 10/058,627, which claims benefit under 35 U.S.C. 119(e) of U.S. provisional patent application 60/264,803, both incorporated by reference herein.

FIELD OF THE INVENTION

This invention relates to a method and apparatus for in vivo intradermal incorporation of microparticles containing an encapsulated drug or other beneficial substance such as a therapeutic agent or cosmetic for topical or subcutaneous application using low-frequency ultrasound.

BACKGROUND OF THE INVENTION

Intradermal delivery of drugs offers several advantages over conventional delivery methods including oral and injection methods. It delivers a predetermined drug dose to a localized area with a controlled steady rate and uniform distribution, is non-invasive, convenient and painless.

U.S. Pat. No. 6,487,447, commonly assigned and incorporated by reference herein, describes a method and apparatus for sonoporation of biological barriers such as Stratum Corneum (SC), most commonly referred to as the outermost layer of human skin. Sonoporation is the noninvasive transdermal delivery of pharmaceutical drug molecules through the SC and into the cardiovascular system a human body via ultrasound radiation. Significant improvement made to existing sonoporation and sonophoresis methods of transdermal drug delivery may be leveraged to increase market share. Drug encapsulation is a known practice in therapeutic application of the potent but very unstable drugs. Using sonoporation and sonophoresis in the area of delivery of encapsulated drugs would provide many additional pharmaceutical benefits compared to the benefits of a present ways of sonoporetic or sonophoresic drug delivery. Some of these benefits would include delivery of peptide-based drugs that range from bed-wetting to gastric bleeding to cancer and immune disorders such as HIV.

SUMMARY OF THE INVENTION

In one aspect, the invention provides for an apparatus for sonoporation for intradermal delivery of a microparticles suspension containing one or more microencapsulated drugs or other beneficial substances including a container having an end covered with a porous membrane and containing the microparticles suspension; an ultrasound horn having a tip submerged in the microparticles suspension and applying ultrasound radiation to the microparticles suspension wherein the ultrasound radiation is applied at a frequency, an intensity, for a period of time, and at a distance from the skin, effective to generate cavitation bubbles, wherein the cavitation bubbles collapse and transfer their energy into the skin area thus causing the formation of pores in the skin area; and wherein the ultrasound radiation intensity and distance from the skin area are also effective in generating ultrasonic jets, the ultrasonic jets driving the microparticles suspension through an optional porous membrane and the formed pores into the skin area.

Implementations of the invention may include one or more of the following features. The porous membranes desirably have pores with a diameter of 100 microns (μm) or greater. Larger pores make it easier for the microparticles suspension to penetrate the membrane. Alternatively, the porous membrane may be microporous; that is, it won't allow liquid to run through without pressure, and typically has pores in the range of about 1 μm to 100 μm. The optional membrane may be hydrophobic.

The ultrasound radiation has a frequency in the range of 1 kHz and 1 MHz. Preferably the frequency is between 5 kHz and 30 kHz. Most preferably it is between 10 kHz and 20 kHz. In a preferred embodiment it is about 20 kHz.

The tip may be removably connected to the ultrasound horn and it may have a distal end surface, which may be flat, concave or it may be open. The distal end surface may have a plurality of depressions. The tip may also have a body having markings indicating the amount of microparticles suspension containing microencapsulated drugs contained in the container or intended to be introduced therein. A removable protective film may cover the membrane, if any; otherwise it directly covers the end of the tip.

The container may include an outer wall, and optionally an inner wall and an absorbent wick placed between the inner and outer wall. The wick absorbs any excess microparticles suspension containing microencapsulated drugs that is not driven into the skin area through the formed pores and it may be made of highly absorbent and hydrophilic material such as PVA sponge CLINICEL™ from M-Pact Company, HYDROFERA PVA sponge from Hydrofera LLC, Sodium CMC and any other similar spongy material. The container inner wall may have first and second grooves and the tip may have a body having first and second grooves. The tip is inserted into the container and placed so that the first and second grooves of the tip body are opposite the first and second grooves of the container inner wall. This arrangement defines the first and second spaces for accommodating the first and second o-rings, respectively. The container may also have an inlet septum for filling it with the solution. The container may be a cylinder made of a transparent material and/or a plastic material.

Optionally at the end of the container, a ring of skin-removable resilient medical adhesive material is provided, which functions as a temporary barrier seal around the area where the microparticles suspension is being applied to the patient's skin while the method of the present invention is being performed. (The term "patient" refers to a human or animal receiving treatment according to the present invention.)

The ultrasound frequency may be for example 20 kHz, and the ultrasound intensity may be in the range of 5 $W/cm^2$ and 55 $W/cm^2$. The tip may have a distal end located at a distance from the membrane in the range of 1 millimeter (mm) to 10 millimeters. The ultrasound radiation may be continuous or pulsed and it may be applied for a period of time in the range of 30 seconds to 5 minutes, preferably 1 minute for continuous exposure or about 10 to 20 minutes for pulsed exposure with a 5% duty cycle, respectively. The formed pores may have a diameter in the range of 1 micrometer (μm) to 100 micrometers.

The microparticles may have an average diameter from 0.1 μm to about 50 μm. For many applications they desirably have an average diameter from 1 μm to 5 μm.

In another aspect, the invention features a method for sonoporation for intradermal delivery of a microparticles suspension containing microencapsulated drug or other beneficial substance such as one or more therapeutic agents or cosmetics. The method includes providing a container containing a predetermined amount of said microparticles suspension, and having a first end and a second end, said second end being covered with a porous membrane. Next the tip of an ultrasound horn is submerged in the microparticles suspension through the first end of the container and then the porous membrane is placed in contact with the patient's skin area. The ultrasound radiation is applied at a frequency, and intensity, for a period of time, and at a distance from the skin, effective to generate cavitation bubbles. The cavitation bubbles collapse and transfer their energy into the skin area thus causing the formation of pores in the skin area. The ultrasound radiation intensity and distance from the skin area are also effective in generating ultrasonic jets, the ultrasonic jets driving the microparticles suspension through a porous membrane and the formed pores into the skin area.

In a further aspect, the ultrasound radiation can then applied at a frequency in the range of 1 kHz and 1 MHz selected to avoid a resonant frequency of the particles. If the ultrasound were at a resonant frequency, it would tend to rupture the particles. A feature of the present invention is that at least a majority of the particles are delivered into the skin area without rupturing them. Preferably substantially all of the particles are delivered intact. For each formulation of particles and application, the preferable frequency may desirably be determined empirically by applying various frequencies to the microparticles suspension and determining at which range of frequencies the particles remain un-ruptured. In general, it has been found that a frequency between 1 kHz and 30 kHz is typically applicable. Most preferably it is between 10 kHz and 20 kHz. In a preferred embodiment it is about 20 kHz.

One advantage of the present invention is to protect against any unknown effects of ultrasound and cavitation on drugs, or therapeutic agents or cosmetics.

A second advantage of the present invention is the controlled release of drugs, or other beneficial substances over time into the stratum corneum and subsequently into the human vascular system. This invention can be used to provide slow and constant intradermal release of drugs, or therapeutic agents or cosmetics, because most or desirably all of the particles delivered into the skin are substantially intact.

A third advantage of the present invention is to reduce the need for repeated dosage of drugs, or therapeutic agents since time-released beneficial substances can be administered once and not require repeating for longer periods of time than dosages required using conventional methods.

A fourth advantage of the present invention is the ability to apply sensitive, non-soluble or unstable beneficial substances. Drugs, or therapeutic agents or cosmetics can be specially engineered to retain full potency in a stable environment within the microparticle until it is delivered using sonoporation. The encapsulation prevents the premature breakdown of drugs or active agents or cosmetic before they can be effectively delivered into or through the skin.

A fifth advantage of the present invention is that the delivery of the drugs and therapeutic agents is painless compared to the side effects or the discomfort and pain associated with injection.

DETAILED DESCRIPTION

The present invention provides an apparatus and method for intradermal incorporation of microparticles containing encapsulated drugs, or therapeutic agents or cosmetics using sonoporation. The apparatus is designed to use ultrasound to deliver a suspension of microparticles into the epidermal layer of the skin. The microparticles contain medication or cosmetic that is encapsulated to provide protection. The encapsulation also provides means of controlled released of the drug, or therapeutic agents or cosmetic into the skin.

Figure 1:
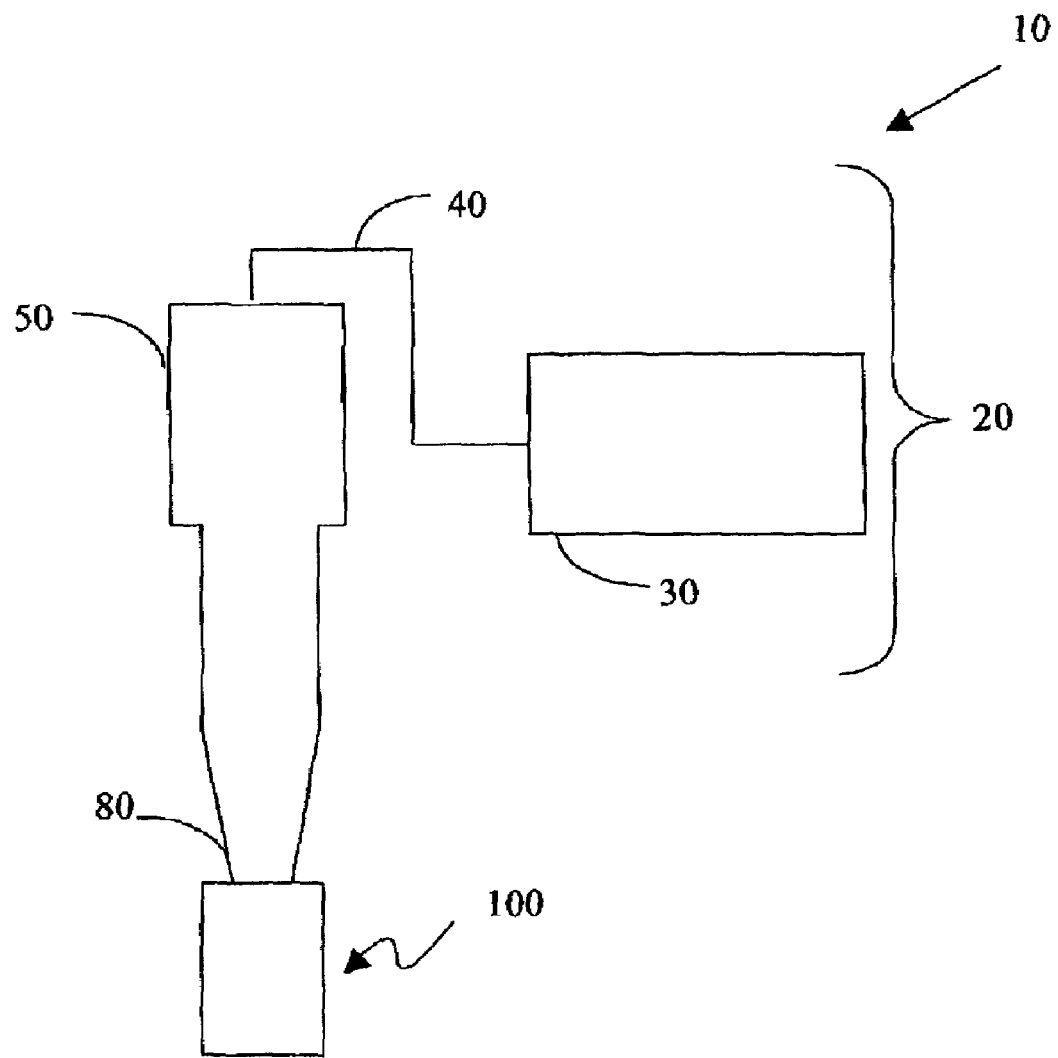
FIG. 1 is a cross sectional side view of an apparatus for intradermal delivery of microparticles using ultrasound.

With reference to the drawings, FIG. 1 shows a sonoporation device 6 used for in vitro sonoporation of skin that includes an ultrasound equipment assembly 20, electrically and mechanically connected to an ultrasonic transdermal drug delivery applicator (UTDDA) 100 (described in detail below) via an ultrasonic horn 80. The ultrasound equipment assembly 20 includes an ultrasound transducer 50, which in turn is electrically connected to power supply 30 via connecting cable 40.

Figure 1A:
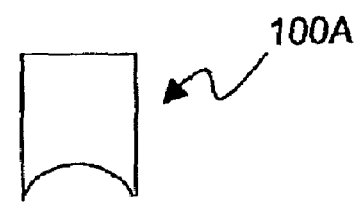
FIG. 1A is a cross sectional side view of an alternative embodiment of the tip, i.e. the UTDDA, shown in FIG. 1.

As shown in FIG. 1, the distal end surface of the UTDDA is flat. As shown in FIG. 1A, the distal end surface of an alternative embodiment of the UTDDA is concave.

In operation, the UTDDA 100 is removably connected to the affected skin surface via pressure resistive adhesive. Ultrasonic horn 80 is placed inside the UTDDA 100. Power supply 30 is activated and provides power to ultrasonic transducer 50. The ultrasonic transducer 50 converts electrical energy into acoustic pressure waves that are coupled through the ultrasonic horn 80 and into the UTDDA 100. Sonoporation of the affected skin occurs for a pre-determined interval, which depending upon skin resistivity and can range from 5 to 60 seconds.

Figure 2:
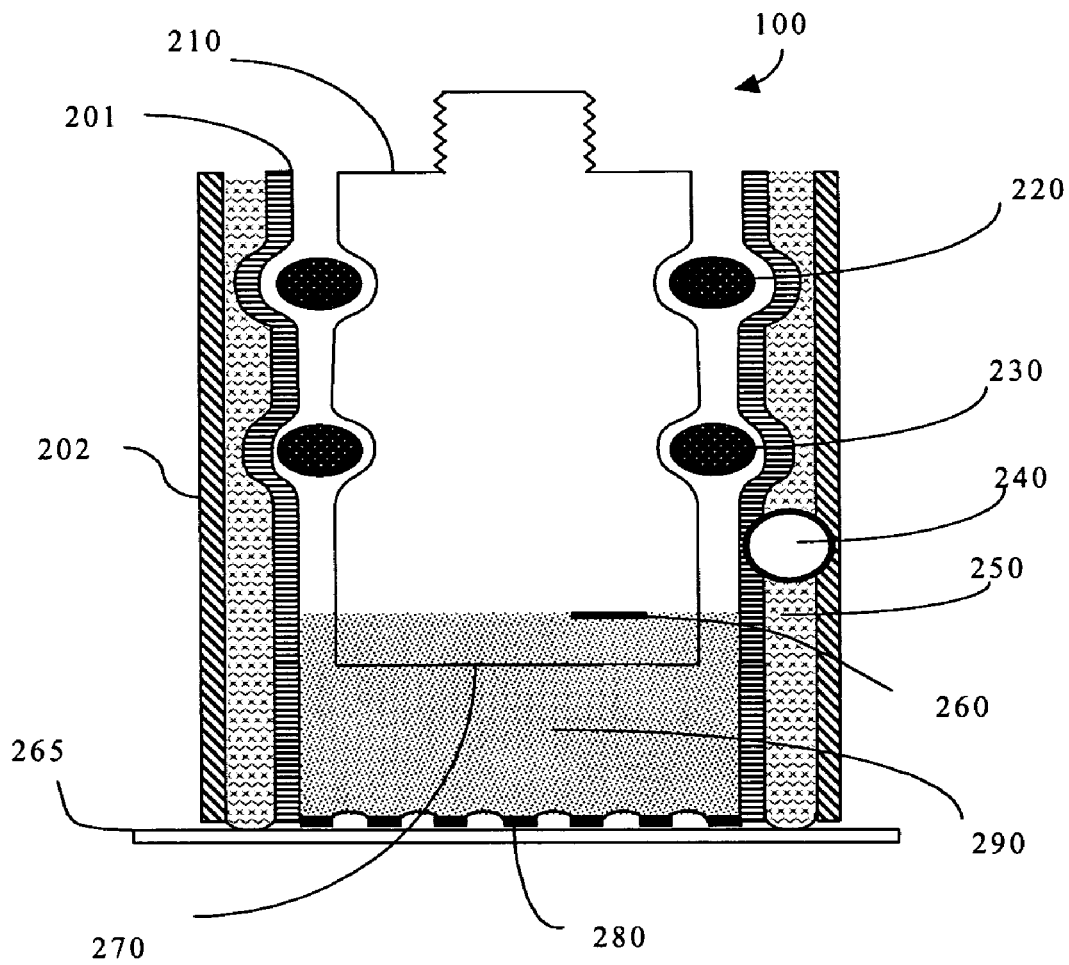
FIG. 2 is a cross sectional side view of an ultrasonic transdermal drug delivery applicator (UTDDA) using microparticles containing encapsulated drugs and therapeutic agents and cosmetics.

FIG. 2 is a schematic of one example of an ultrasonic transdermal drug delivery applicator (UTDDA) 100 in accordance with the invention that includes an inner applicator wall 201, an outer applicator wall 202, a first O-ring 220, a second O-ring 230, a wick 250, a microparticles suspension inlet septum 240, a solution level marking 260, a removable protective film 265, a porous membrane 280, a microparticles suspension 290 that includes microparticles containing encapsulated drugs. FIG. 2 also shows parts of the ultrasonic horn (element 80 of FIG. 1), including a tip of ultrasonic horn 210, and a bottom of ultrasonic horn tip 270.

The UTDDA 100 is a hollow cylindrically shaped object, preferably made of a transparent hard plastic material and is discarded after use. Between the outer applicator wall 202 and the inner applicator wall 201 is a wick 250, made of material such as high-absorbency polypropylene. Both the inner and outer applicator walls 201 and 202 are basically cylindrical and axially aligned, with the exception of two locations on the inner applicator wall 201 where two grooves are cut on the inside surface of the inner applicator wall 201 for the two O-rings 220 and 230 to fit into the assembly. The location and orientation of the grooves, and the two O-rings 220 and 230 are shown in FIG. 2. As shown in FIG. 2, grooves cut into the outer diameter of the ultrasonic horn are matched to the placement of the O-rings 220 and 230 to facilitate a secure fit between the UTDDA 100 and the ultrasonic horn 80.

Again in reference to FIG. 2, the drug inlet septum 240 is located between the outer applicator wall 202 and the inner applicator wall 201 approximately halfway between the top and bottom of the UTDDA 100. The septum is constructed of a silicon rubber material, designed to be impervious to liquids yet allow injection of the microparticles suspension into the UTDDA 100 using a hypodermic needle. The solution marking level 260 is pre-marked on the side of the UTDDA 100 to indicate the proper volumetric measure of microparticles suspension to be administered.

At the base of the UTDDA 100, the porous membrane 280 is fixedly attached to the inner applicator wall 201. The membrane 280, constructed of a non-woven polypropylene or other similar hydrophobic material, resists the passage of the aqueous liquid due to its non-wettable surface and small diameter of the pores in range of 1-100 microns. A removable protective film 265, which is preferably a thin plastic sheet, is removably connected to the porous membrane 280 using silicone or other medical adhesive.

In operation, the sterilized UTDDA 100 is placed over the tip of ultrasonic horn 210 with the two O-rings 220 and 230 in place as shown in FIG. 2. The microparticles suspension 290 with suspended microparticles containing encapsulated drugs is introduced into the reservoir of the UTDDA 100 through the inlet septum 240 using a hypodermic needle (not shown) to inject a pre-measured amount of microparticles suspension 290. The protective film 265 is peeled off to expose the porous membrane 280. When the UTDDA 100 is properly filled, the tip of the ultrasonic horn 210 is partially immersed in the microparticles suspension 290. Visual inspection of the solution level marking 260 indicates whether the applicator is properly filled, and whether the UTDDA 100 is leaking or defective.

Once the UTDDA 100 is filled and determined to be ready for use, the apparatus is placed on the skin, oriented such that the porous membrane 280 is flush with the location where the drugs are to be administered and such that the bottom of the horn tip 270 is immersed in microparticles suspension 290. A timer (not shown), which is contained in power supply 30, is set to a predetermined length of time for sonoporation. The power supply is switched on, and the ultrasound sonoporates the skin for an allotted amount of time. The porous membrane 280 is designed to prevent the microparticles suspension from leaking prior to transdermal infusion process, yet simultaneously allow ultrasound waves to freely pass through the membrane 280 and sonoporate the skin surface. Any excess liquid that is transferred to the skin during the ultrasound exposure is absorbed by the wick 250. After use, the UTDDA 100 is removed form the ultrasound tip and discarded.

Figure 3:
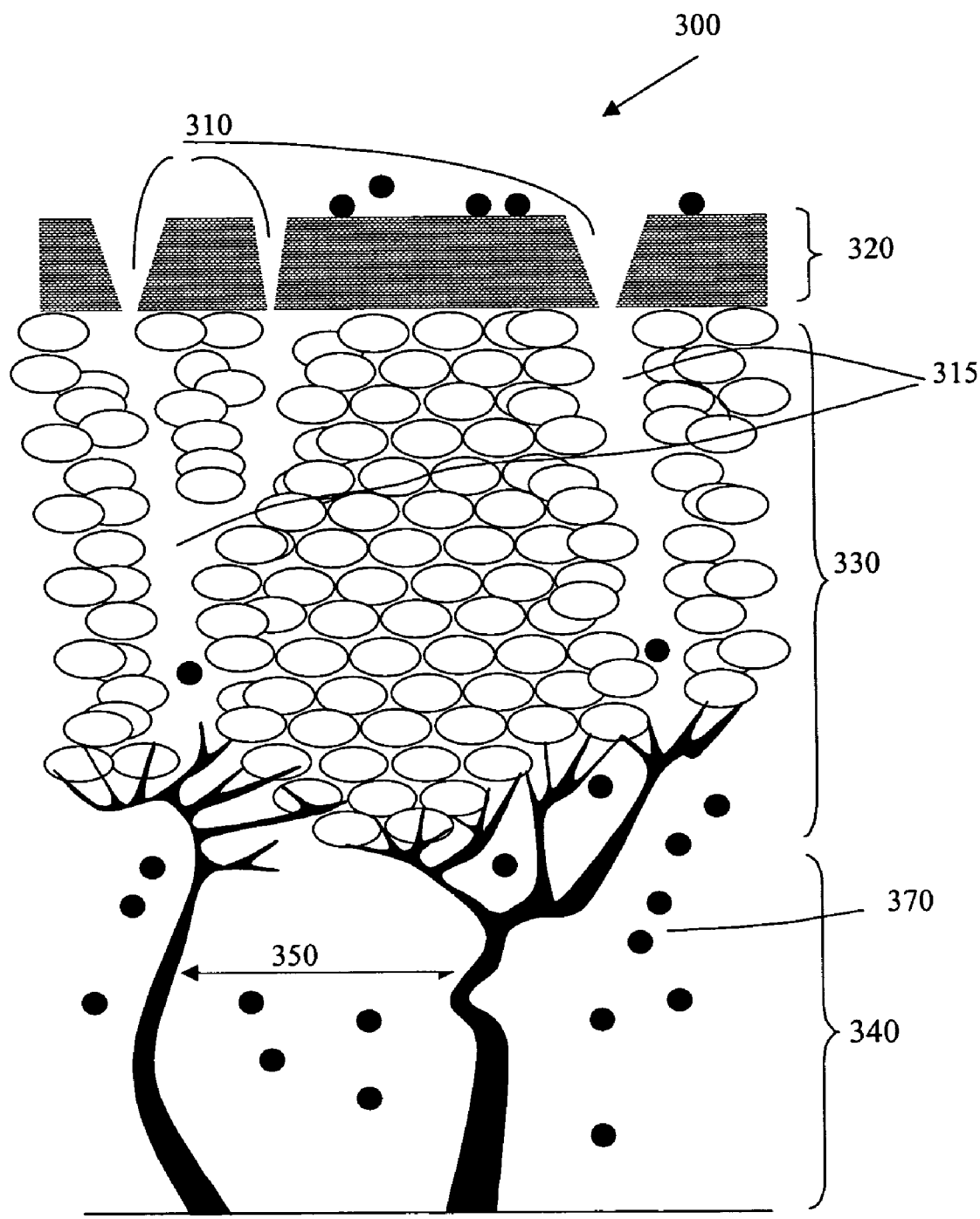
FIG. 3 is a graphic transcription of the confocal microscopy image of the cross-section of the upper part of the skin after 15 seconds exposure to 20 kHz ultrasound at intensity of 19 W/cm$^2$ in aqueous suspension of 1 µm particles.

FIG. 3 shows a skin system 300 that represents a cross section of human skin after exposure to 20 kHz ultrasound in presence of the suspension of the 1 μm particles in aqueous saline solution. The figure shows the environment where the drug, therapeutic agent, or cosmetic, which is encapsulated in the microparticle is delivered into the skin by action of the 20 kHz ultrasound. The cross-section of the skin includes a stratum corneum (the top part of the skin) 320, an underlying layer called the viable epidermis 330, and a dermis 340. Between the epidermal and dermal layers reside the endings of a capillary vascular system 350. Pores 310 in the stratum corneum 320 and the transient micropores 315 in the viable epidermis 330 are created when the skin is exposed to ultrasound. The size of the pores in stratum corneum is in the range of 1 to 100 micrometers in diameter. The size of the micropores generated in viable epidermis is in range up to 35 micrometers in diameter. The ultrasound intensity is in the range of 11 W/cm to 79 W/cm The figure shows the microparticles 370 migrating through the pores 310 in the stratum corneum 320 then through the transient micropores 315 in the viable epidermis 330 to part of the dermis with the capillary vascular system 350.

In operation, the microparticles suspension 290 containing the microparticles 370 is delivered to the skin using the sonoporation apparatus. The ultrasound assists in propelling the microparticles 370 through the pores 310 and transient micropores 315. Once the microparticles are lodged in the epidermis, the drug, or therapeutic agent, or cosmetic is released from the microparticles at a controlled rate determined by the microparticle chemical composition. Subsequently the drug, or therapeutic agent released from the microparticles is ultimately absorbed into the capillary vascular system 350.

Figure 4:
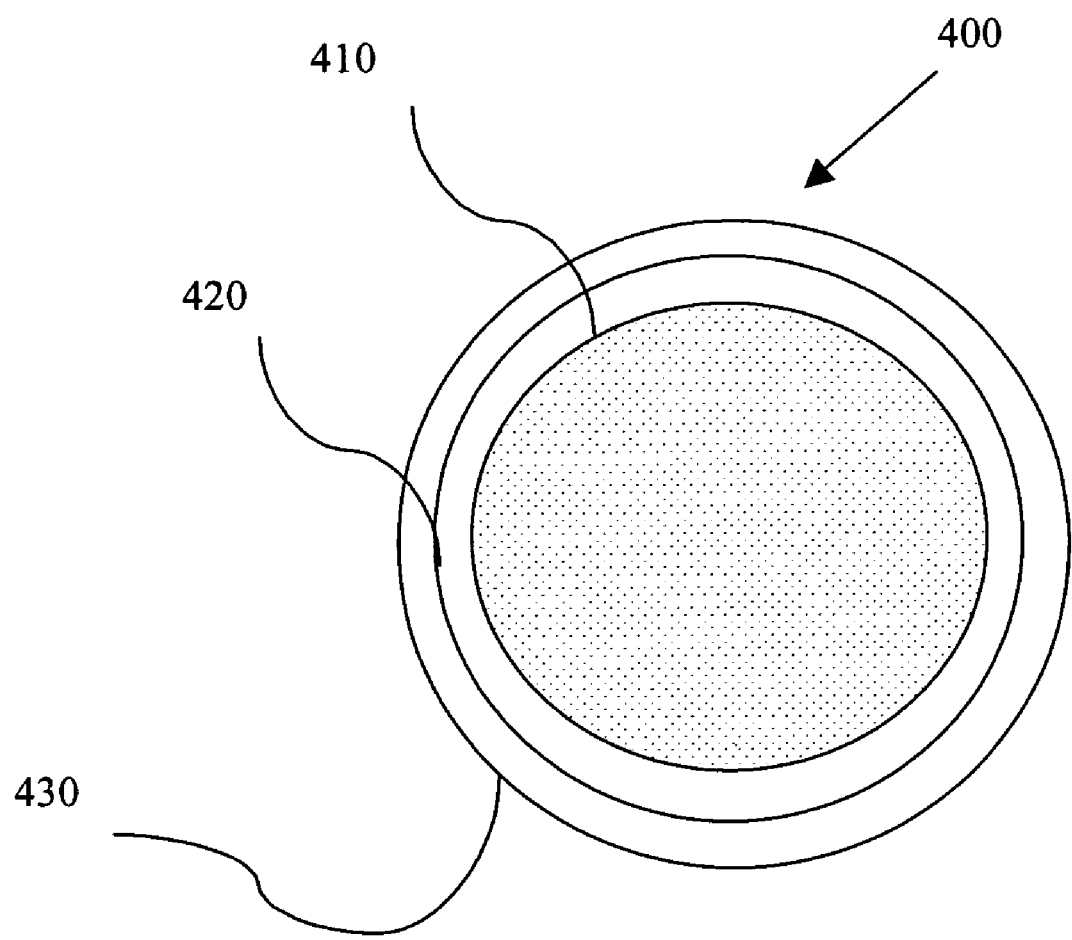
FIG. 4 is a cross sectional of a microparticle containing encapsulated drugs, or therapeutic agents or cosmetics.

FIG. 4 shows a schematic of a cross-section of a microparticle 400 containing a drug, or therapeutic agent, or cosmetic 410, a first protective sheath 420, and a second protective sheath 430. Microencapsulation is a known process in the pharmaceutical field and is not described here. Examples of other patents that address the method of creating and using microparticles include U.S. Pat. No. 4,983,401, U.S. Pat. No. 5,792,477, U.S. Pat. No. 5,723,269, U.S. Pat. No. 6,048,550, and U.S. Pat. No. 5,651,990. The microparticle 400 is generally spherical and includes one or more protective sheaths, arranged in concentric and incrementally smaller hollow spheres, with a center core sphere of encapsulated drug, or therapeutic agent, or cosmetic in a solid, liquid or solvated states. The content of encapsulated drugs, or therapeutic agent, or cosmetic 410 is shown in FIG. 4 at the center of the microparticle 400.

In one example embodiment, drug or a therapeutic agent 410 includes anti-fungal agents, hormones, vitamins, peptides, enzymes, anti-allergic agents, anti-coagulation agents, antituberculars, antivirals, antibiotics, antibacterials, antiinflammatory agents, antiprotozoans, local anesthetics, growth factors, cardiovascular agents, diuretics, and radioactive compounds; scopolamine, nicotine, methyinicotinate, mechlorisone dibutyrate, naloxone, methanol, caffeine, salicylic acid, and 4-cyanophenol; anti-fungal agents selected from the group consisting of ketoconazole, nystatin, griseofulvin, flucytosine, miconazole, and amphotericin B; hormones selected from the group consisting of growth hormone, melanocyte stimulating hormone, estradiol, progesterone, testosterone, bcclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide and fludrocortisone acetate; vitamins selected from the group consisting of cyanocobalamin neinoic acid, retinoids, retinol palmitate, ascorbic acid, and alpha-tocopherol, B-12 and other vitamins; peptides and enzymes selected from the group consisting of manganese super oxide dismutase and alkaline phosphatase; the anti-allergic agent is amelexanox; the anti-coagulation agents selected from the group consisting of phenprocoumon and heparin; the antituberculars selected from the group consisting of paraminosalicylic acid, isoniazid, capreomycin sulfate cycloserine, ethambutol hydrochloride ethionamnide, pyrazinamide, rifampin, and streptomycin sulfate; the antivirals selected from the group consisting of acyclovir, amantadine azidothymidine, ribavirin and vidarabine monohydrate; the antibiotics selected from the group consisting of dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin rifampin and tetracycline; the antiinflammatories selected from the group consisting of diflunisal, ibuprofen, indomethacin, meclofenamate, mefenamic acid, naproxen, oxyphenbutazone, phenylbutazone, piroxicam, diclofenac, sulindac, tolmetin, aspirin and salicylates; the antiprotozoans selected from the group consisting of chloroquine, hydroxychloroquine, metronidazole, quinine and meglumine antimonate; the local anesthetics selected from the group consisting of bupivacaine hydrochloride, chloroprocaine hydrochloride, etidocaine hydrochloride, lidocaine hydrochloride, mepivacaine hydrochloride, procaine hydrochloride and tetracaine hydrochloride; the growth factors selected from the group consisting of Epidermal Growth Factor, acidic Fibroblast Growth Factor, Basic Fibroblast Growth Factor, Insulin-Like Growth Factors, Nerve Growth Factor, Platelet-Derived Growth Factor, Stem Cell Factor, Transforming Growth Factor of the alpha family and Transforming Growth Factor of the beta family; the cardiovascular agents are selected from the group consisting of clonidine, propranolol, lidocaine, nicardipine and nitroglycerin; the diuretics are selected from the group consisting of mannitol and urea; and wherein the radioactive particles are selected from the group consisting of strontium, iodine, rhenium and yttrium.

In another example embodiment, therapeutic agent 410 includes the following:
(1) peptides selected from the group consisting of melanin concentrating hormone, melanin stimulating hormone, trypsin inhibitor, Bowman Burk inhibitor, luteinizing hormone releasing hormone, bombesin, cholecystokinin, insulin, gastrin, endorphins, enkephalins, growth hormone, prolactin, oxytocin, follicle stimulating hormone, human chorionic gonadotropin, corticotropin, .beta.-lipotropin, .gamma.-lipotropin, calcitonin, glucagon, thyrotropin, elastin, cyclosporin, and collagen;
(2) monoclonal antibodies;
(3) factors selected from the group consisting of hyaluronic acid, heparin, mad heparin sulfate;
(4) anti-sense peptides and anti-sense oligonucleotides selected from the group consisting of an antisense oligonucleotide capable of binding the DNA encoding at least a portion of Ras, an antisense oligonucleotide capable of binding the DNA encoding at least a portion of basic fibroblast growth factor, and the antisense ras/p53 peptide;
(5) immunosuppressants and anti-inflammatory agents;
(6) chelants and chelating agents selected from the group consisting of penicillamine, citrate, ascorbate, diethylenetriaminepentaa-cetic acid, dihydroxypropylethylenediamine, cyclohexanediaminetetraacetic acid, ethylenediaminetetraacetic acid, ethylene glycol-bis (.beta.-aminoethyl ether)N,N,N',N',-tetraacetic acid, etidronic acid, dimethylsulfoxide, dipyridoxylethylenediaminediacetate-bisphosphate, N,N'-(1,2-ethanediylbis(oxy-2,1-phenylene))bis(N-(carboxymethyl), aminophenoltriacetic acid, tetrakis(2-pyridylmethyl) ethylenediamine, cyanins, and salts thereof; and
(7) DNA encoding at least a portion of the following genes: HLA, dystrophin, CFTR, interleukin-2, tumor necrosis factor, adenosine deaminase, HDL receptor, thymidine kinase, HLA-B7, interleukin-4, melanocyte stimulating hormone gene, and melanin concentrating hormone gene.

In yet another example embodiment, the cosmetic 410 includes Vitamin A, Vitamin C, Vitamin D, Vitamin E, Vitamin K, beta carotene, collagen, elastin, retinoic acid, aloe vera, lanolin, hyaluronic acid, and nucleosides; a sunscreen agent, said sunscreen agent selected from the group consisting of 5% isobutyl-p-aminobenzoate, 5% diallyl trioleate, 2.5% monoglyceryl p-aminobenzoate, 4% propylene glycol p-aminobenzoate, and a composition comprising 2% benzyl salicylate and 2% benzyl cinnamate; a cosmetic cream, ointment, lotion, skin softener, gel, blush, eye-liner, mascara, acne-medication, cold cream, cleansing cream, or oleaginous foam.

In another example embodiment, the composition 410 comprises one or more compounds selected from the following:
(1) bacteriostatic agents selected from the group consisting of benzalkonium chloride, benzethonium chloride, benzoic acid, benzyl alcohol, butylparaben, cetylpyridinium chloride, chlorobutanol, chlorocresol, methylparaben, phenol, potassium benzoate, potassium sorbate, sodium benzoate and sorbic acid;
(2) antioxidants selected from the group consisting of tocopherol, ascorbic acid and ascorbyl palmitate;
(3) preservatives selected from the group consisting of parabens, quaternary ammonium compounds, alcohols, phenols, and essential oils;
(4) buffers and neutralizers;
(5) moisture content control agents and humectants;
(6) ointment bases selected from the group consisting of lanolin, lanolin anhydrous, hydrophilic ointment, white ointment, yellow ointment, polyethylene glycol ointment, petrolatum, hydrophilic petrolatum, white petrolatum, rose water ointment, and squalene;
(7) suspending and viscosity-increasing agents selected from the group consisting of acacia, agar, alginic acid, aluminum monostearate, bentonite, purified bentonite, magma bentonite, carbomer 934P, carboxymethylcellulose calcium, carboxymethylcellulose sodium 12, carboxymethylcellulose sodium, carrageenan, microcrystalline cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, silicon dioxide, zinc oxide, sodium alginate tragacanth, and xanthan gum;
(8) skin absorption enhancing agents selected from the group consisting of pyrrolidones, fatty acids, sulfoxides, amines, terpenes, terpenoids, surfactants, alcohols, urea, glycols, azone, n-alkanols, n-alkanes, orgelase, and alphaderm cream;
(9) bases selected from the group consisting of glycerol, propylene glycol, isopropyl myristate, urea in propylene glycol, ethanol and water, and polyethylene glycol;
(10) other agents selected from the group consisting of glycerin, hexylene glycol, sorbitol, propylene glycol, and calcium silicate;
(11) oleaginous vehicles;
(12) coloring agents; and
(13) foaming agents.

In another example embodiment, the composition 410 comprises a gas in range of 0-50% in the interior of the microparticle and an effective amount of drug, or therapeutic agent, or cosmetic.

A structural composition of the microparticle 370 or 400 can vary depending on the content of the microparticle and the method of the release of that content once the microparticles are embedded in the skin.

In one example embodiment microparticle 370 or 400 includes liposomes, microspheres, nano-spheres or nanoparticles. In another example embodiment microparticle 370 or 400 consists of first protective layer 420 as the next largest hollow sphere, and second protective layer 430 as outermost hollow sphere. This design may consist of one, two, or as many protective layers as required for a given microparticle structural composition.

The layers of the microparticle's structure includes but is not limited to lipid conglomerates or polymers preferably biodegradable.

In another example embodiment microparticle 370 or 400 is prepared from at least one biocompatible lipid. In another example embodiment microparticle 370 or 400 is prepared from at least one biocompatible polymer selected from the group consisting of polysaccharides, semi-synthetic polymers and synthetic polymers. In another example embodiment microparticle 370 or 400 is prepared from the following:
(1) from a composition comprising dipalmitoylphosphatidylcholine, glycerol and propylene glycol.
(2) from a composition comprising dipalmitoylphosphatidylethanolamine and phosphatidic acid in an amount of from 0.5 to 30 mole percent.
(3) from a composition comprising dipalmitoylphosphatidylcholine and distearoylphosphatidyl-choline in an amount of from 70 to 100 mole percent.
(4) from a composition comprising: (I) a neutral lipid, (ii) a negatively charged lipid, and (iii) a lipid bearing a hydrophilic polymer; wherein the amount of said negatively charged lipid is greater than 1 mole percent of total lipid present, and the amount of lipid bearing a hydrophilic polymer is greater than 1 mole percent of total lipid present.

In another example embodiment microparticle 370 or 400 comprises the following:
(1) a mono-layer.
(2) a polymer.
(3) a polysaccharide.
(4) a micelle system.
(5) a surfactant.

In operation, the microparticles 400 are forced into the ultrasonically disrupted skin as shown in FIG. 3. After the particle is embedded in the dermis, the protective layer or layers surrounding the drugs, or therapeutic agents, or cosmetic are released into the skin in one or more of the following manners:
(1) the microparticle dissolves or biodegrades in the skin with predetermined rate and the drugs, or therapeutic agents, or cosmetic are released The rate of dissolution will depend on the design of the protective sheath and the number of sheaths surrounding the center core of the microparticle.
(2) The microparticles containing gas in their interior are burst open by application of an additional external ultrasound of an resonance frequency that matches the size of the microparticles containing gas along with a drug, or therapeutic agent, or cosmetic. For example, when diameter of the gas containing microparticle is 3 micrometers, which is convenient size for drug, or therapeutic, or cosmetic carrier, the resonance frequency is 2.2 MHz. By the large-amplitude vibration and the rise of the temperature caused by the resonance, the drug, or therapeutic agent, or cosmetic is released in to the skin.

Figure 5:
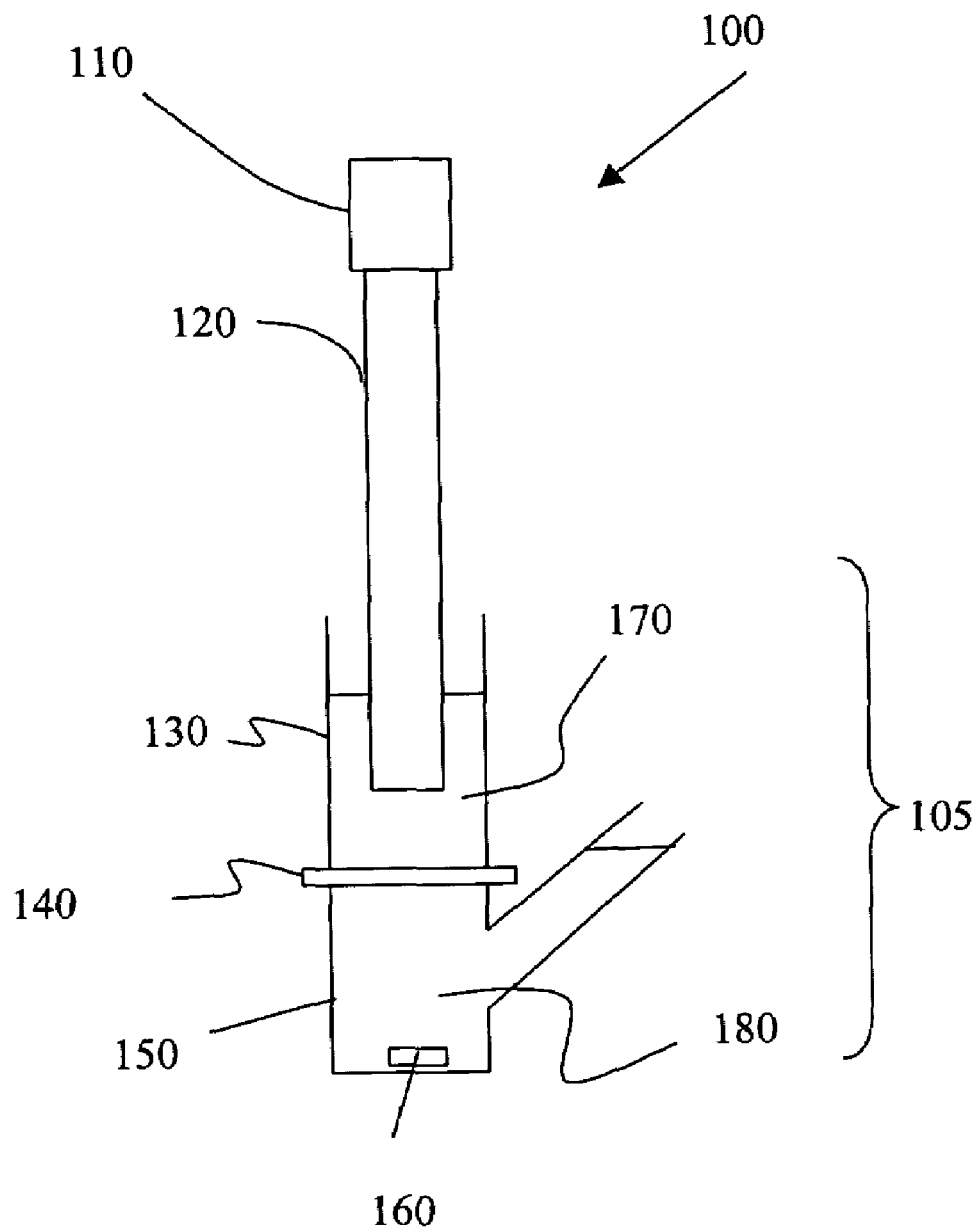
FIG. 5 is a cross sectional side view of a Franz Cell apparatus for determining infusion of microparticles into the human cadaver epidermis.

FIG. 5 shows Franz Cell apparatus 100 for determining infusion of microparticles into the human cadaver epidermis 140 during exposure of the skin to ultrasound of 20 kHz and intensity of 19 W cm.sup.-2. The apparatus 100 includes the ultrasound transducer 110 with horn 120 and Franz Cell assembly 105. The ultrasound horn 120 is electrically and mechanically connected to an ultrasound transducer 110. Ultrasound transducer 110 is electrically connected to a power supply (not shown). The ultrasound horn 120 is submerged in the microparticles suspension 170 placed in the donor compartment 130. The exposure of the skin to the ultrasound causes formation of pores in the stratum corneum and transient micro-pores in the epidermis of the skin 140, which allow for transdermal flux of the microparticles from the donor compartment 130 to the saline solution 180 in the receiver compartment 150.

Figure 6:
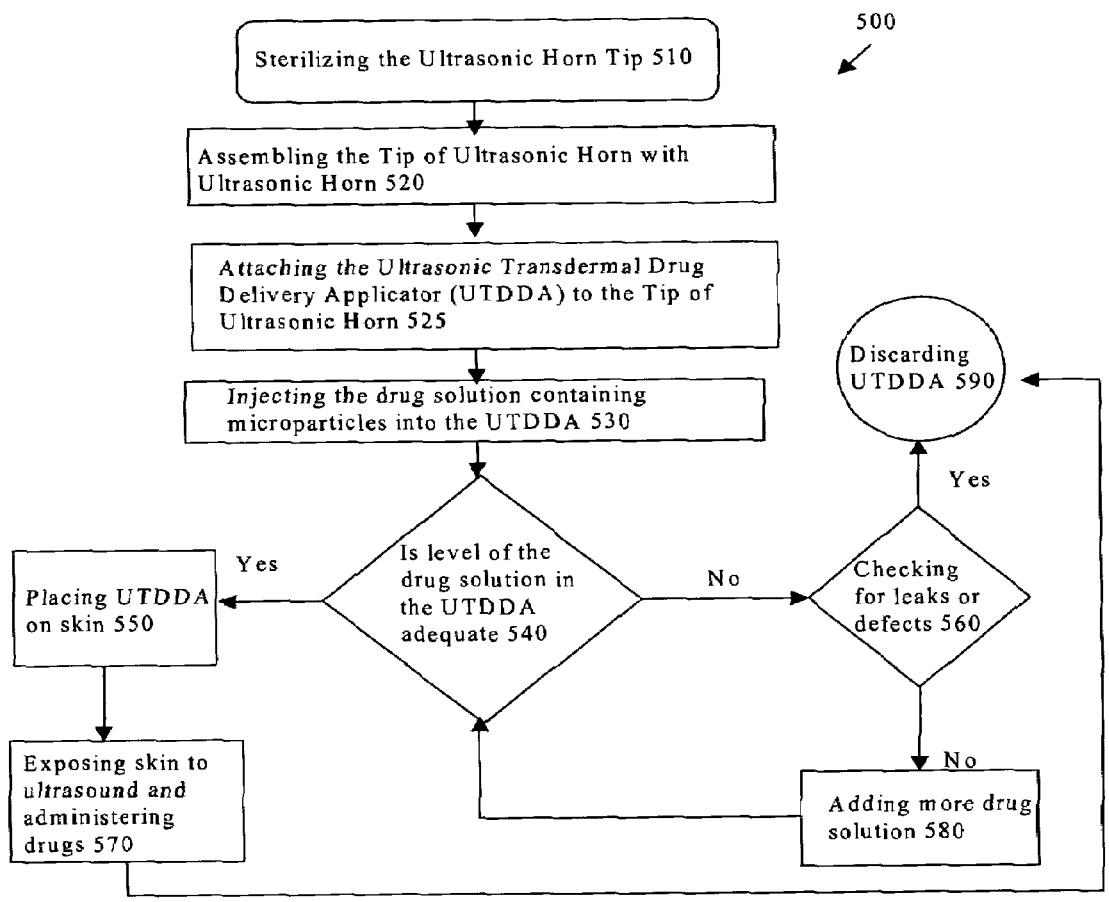
FIG. 6 is a flow chart of a method for transdermal incorporation of microparticles containing encapsulated substance using 20 kHz ultrasound.

FIG. 6 is a method 500 for transdermal incorporation of microparticles containing encapsulated drugs using sonoporation that includes the following steps:

Step 510: Sterilizing the Ultrasonic Horn Tip

The ultrasonic horn tip 270 may be sterilized using an ethylene oxide gas or by exposing the horn tip 270 to elevated heat/steam. The horn tip may also be pre-sterilized and sealed in a protective package. The method then proceeds to Step 520.

Step 520: Assembling the Tip of Ultrasonic Horn with Ultrasound Horn

The sterilized ultrasonic horn tip 270 is attached to the ultrasound horn 80 by screwing the threaded tip into the ultrasound horn. The method then proceeds to Step 525.

Step 525: Attaching the Ultrasonic Transdermal Drug Delivery Applicator (UTDDA) to the Tip of Ultrasonic Horn The tip of the ultrasonic horn 270 is inserted into the UTDDA 100 so that the O-rings 220 and 230 hold the assemblies together securely. The method then proceeds to Step 530.

Step 530: Injecting the Microparticles Suspension Containing Microparticles into the UTDDA The microparticles suspension 290 is introduced into the UTDDA 100 via the septum 240 using a hypodermic needle to inject the solution. The method then proceeds to Step 540.

Decision Step 540: Is Level of the Microparticles Suspension in the UTDDA Adequate By visual inspection, the injected liquid level is compared to the level marking 260. If the microparticles suspension level is aligned with the marked level 260, the method proceeds to Step 550. If the levels are not aligned, the method proceeds to Step 560 to check for the source of inadequate solution level.

Step 550: Placing UTDDA on Skin

The removable protective film 265 is removed from the UTDDA 100. Then the apparatus is oriented such that the porous membrane is fully flush with the skin surface (it must be basically perpendicular to the plane of the skin surface and arranged so that the tip of the horn 270 is immersed in the microparticles suspension 290). The method then proceeds to Step 570.

Decision Step 560: Checking for Leaks or Defects

If the microparticles suspension level is inadequate, the apparatus may be leaking or is defective. The apparatus is visually inspected to look for leaks or visible defects. If there are no other sources of error, the amount of solution may be inadequate to fill the reservoir, and the method proceeds to Step 580 to correct this problem. If the UTDDA 100 is leaking or is otherwise defective, the method proceeds to Step 590.

Step 570: Exposing Skin to Ultrasound and Administering Drugs

The power supply 30 is turned on and a timer, which is contained in power supply 30, is set to a predetermined length of ultrasound exposure (5-60 seconds). The ultrasound is turned on for a predetermined period of time that causes formation of the micropores 310 in the skin and subsequent transfer of the drug from the reservoir of the UTDDA 100 into the micropores formed. The method then proceeds to Step 590.

Step 580: Adding More Microparticles Suspension

If an inadequate volume of solution was initially added to the reservoir, more microparticles suspension 290 is added via the septum. The method then proceeds to Step 540.

Step 590: Discarding UTDDA

If the UTDDA 100 is defective, the applicator must be discarded and a new one used to administer the microparticles suspension 290. After the UTDDA 100 has been used once, it must be discarded. Prior to discarding the UTDDA 100, the power supply is set to a stand-by condition. The method ends after the UTDDA 100 has been discarded.

If the microparticles embedded in the skin are to be burst open in order to release the content into the skin, the external ultrasound of the resonance frequency is applied to skin.

Figure 7:
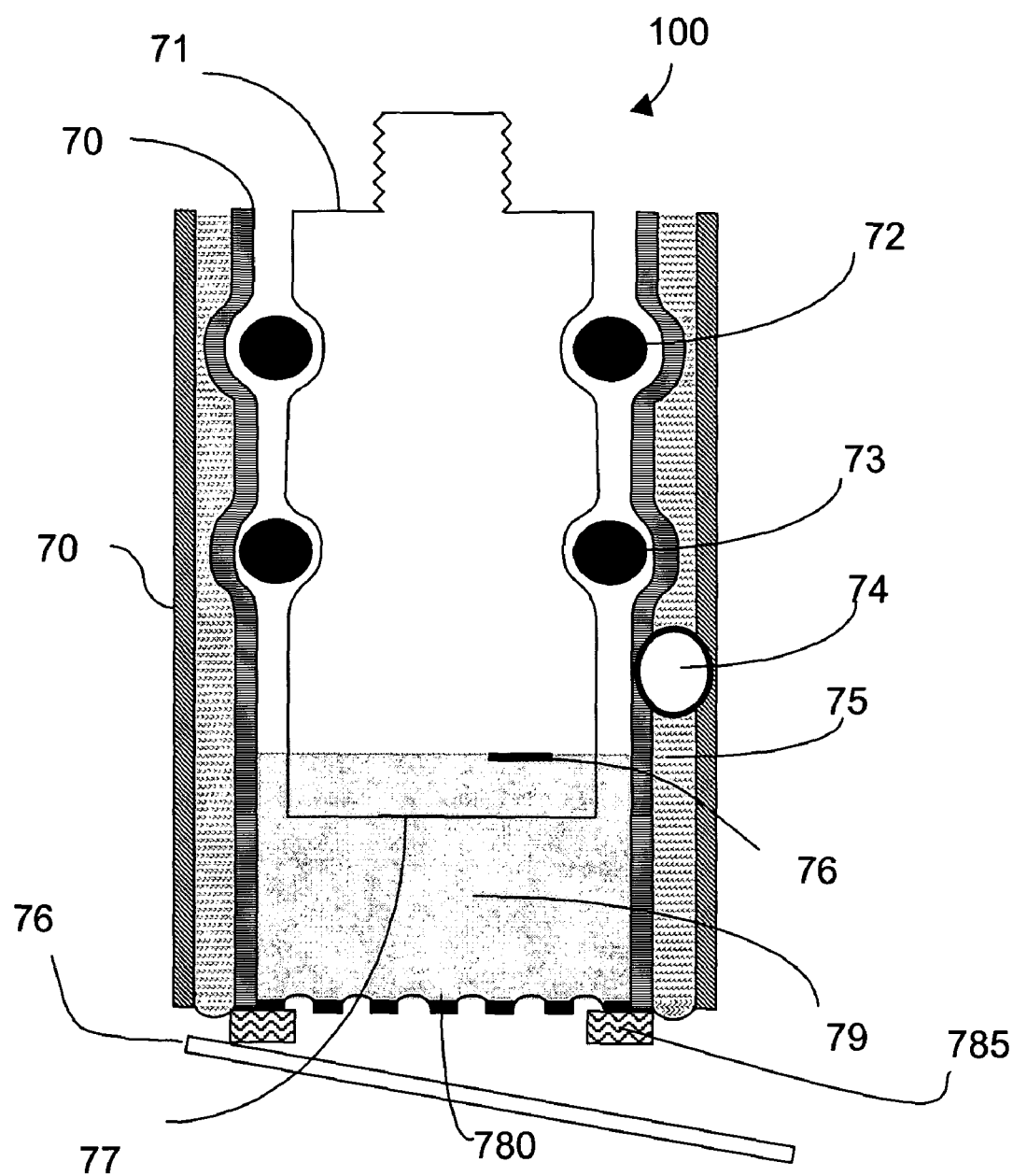
FIG. 7 is a view similar to FIG. 2 of an alternative embodiment of a UTDDA having an adhesive ring thereon.

FIG. 7 is a schematic of another example of an ultrasonic transdermal drug delivery applicator (UTDDA) 100B in accordance with the invention. It includes an inner applicator wall 701, an outer applicator wall 702, a first O-ring 720, a second O-ring 730, a wick 750, a microparticles suspension inlet septum 740, a solution level marking 760, a removable protective film 765, here shown partially removed, a porous membrane 780, and a microparticles suspension 790 that includes microparticles containing encapsulated drugs. The figure also shows parts of the ultrasonic horn (element 80 of FIG. 1), including a tip of ultrasonic horn 710, and a bottom of ultrasonic horn tip 770.

The UTDDA 100B is a hollow cylindrically shaped object, of construction similar to that described above with respect to FIG. 2. Between the outer applicator wall 702 and the inner applicator wall 201 is a wick 750, made of material such as high-absorbency polypropylene. Both the inner and outer applicator walls 701 and 702 are basically cylindrical and axially aligned, with the exception of two locations on the inner applicator wall 701 where two grooves are cut on the inside surface of the inner applicator wall 701 for the two O-rings 720 and 730 to fit into the assembly. The location and orientation of the grooves, and the two O-rings 770 and 730 are shown in FIG. 7. As shown in FIG. 7, grooves cut into the outer diameter of the ultrasonic horn are matched to the placement of the O-rings 720 and 730 to facilitate a secure fit between the UTDDA 100B and the ultrasonic horn 80.

Again in reference to FIG. 7, the drug inlet septum 740 is located between the outer applicator wall 702 and the inner applicator wall 701 approximately halfway between the top and bottom of the UTDDA 100B. The septum is constructed of a silicone rubber material, designed to be impervious to liquids yet allow injection of the microparticles suspension into the UTDDA 100B using a hypodermic needle. The solution marking level 760 is pre-marked on the side of the UTDDA 100B to indicate the proper volumetric measure of microparticles suspension to be administered.

At the base of the UTDDA 100B, the porous membrane 780 is fixedly attached to the inner applicator wall 701. The membrane 780, constructed of a non-woven polypropylene or other similar hydrophobic material, resists the passage of the aqueous liquid due to its non-wettable surface and small diameter of the pores in range of 1-100 microns (μm). A removable protective film 765, which is preferably a thin plastic sheet, is removably connected to the porous membrane 780 by a ring 785 of medical adhesive which has two purposes.

The first purpose of the adhesive ring 785 is to adhere the protective film 765 to the base of the UTDDA 100B. The second purpose is to form a seal when the UTDDA 100B is applied to the patient's skin, preventing leakage of fluid into the surroundings.

The adhesive ring 785 may be composed, for example, of an acrylic adhesive such as DuraTak 87-2516, Duratack 87-2353 or Duro-Tak 87-4098 (National Starch) or Gelva 737, Gelva 1151, or Gelva 1430 (Solutia). Alternatively the adhesive ring may be composed, for example, of a rubber-type adhesive such as Duro-Tak 87-6430 or Duro-Tak 87-6173 (National Starch). Alternatively the adhesive ring may be composed of a silicone adhesive such as MED-1356, MED 6345 or MED6340 (NuSil) or BIO-PSA 4301 or BIO-PSA 4601.

In operation, the sterilized UTDDA 100B operated substantially as described above with respect to UTDDA 100. However, after the protective film 765 is peeled away as shown, the adhesive ring 785 is exposed at the bottom of UTDDA 100B so as to be placed in contact with the patient's skin and form a temporary seal thereto. Any fluid which nevertheless spills out from the region of the seal is absorbed by the wick 750. After use, the UTDDA 100B is removed form the ultrasound tip and discarded.

FIG. 8 is a schematic of another example of an ultrasonic transdermal drug delivery applicator (UTDDA) 100B in accordance with the invention. It includes an inner applicator wall 801, an outer applicator wall 802, a first O-ring 820, a second O-ring 830, a wick 850, a microparticles suspension inlet septum 840, a solution level marking 860, a removable protective film 865, here shown partially removed, a porous membrane 880, and a microparticles suspension 890 that includes microparticles containing encapsulated drugs. The figure also shows parts of the ultrasonic horn (element 80 of FIG. 1), including a tip of ultrasonic horn 810, and a bottom of ultrasonic horn tip 870.

Figure 8:
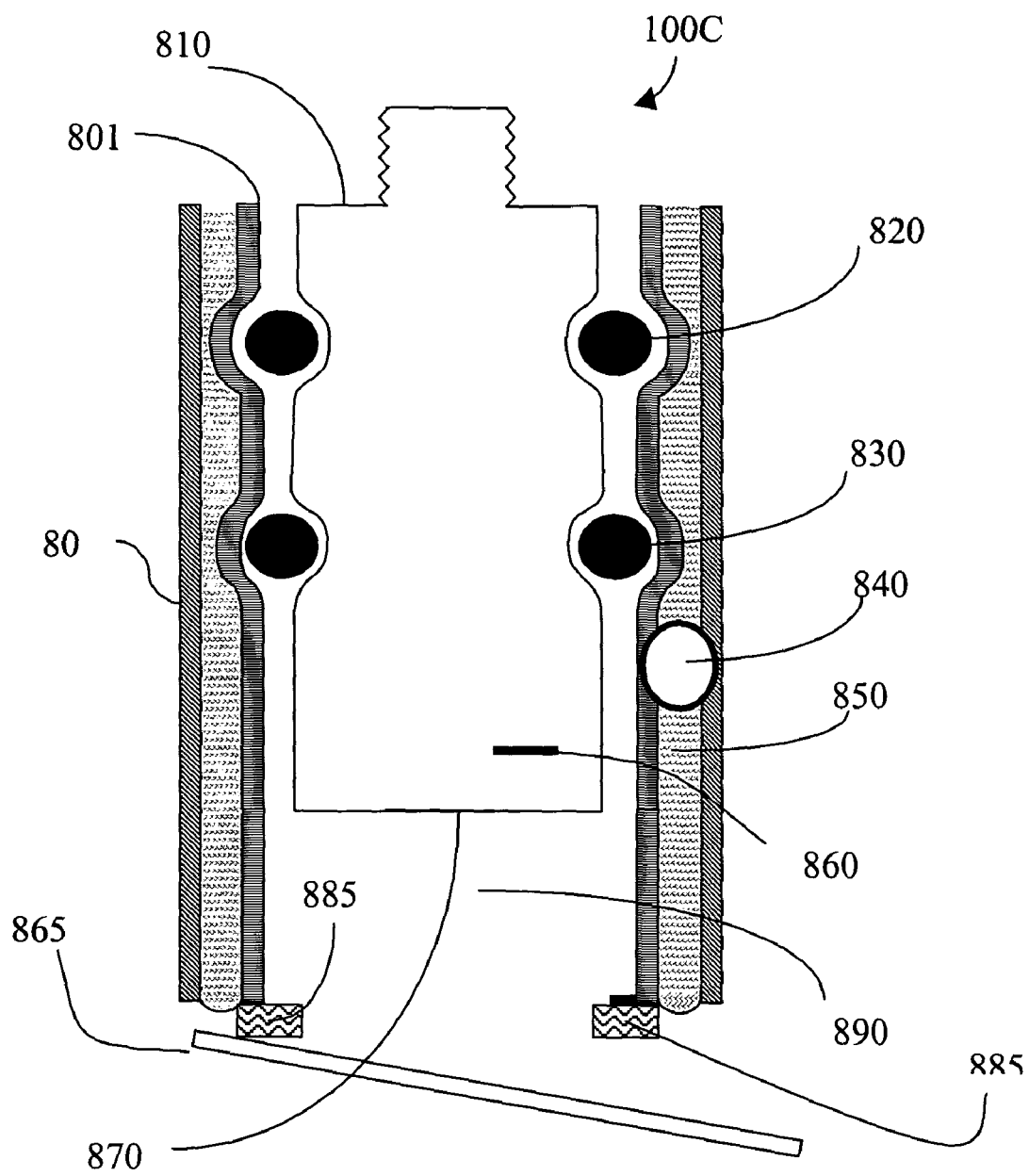
FIG. 8 is a view similar to FIG. 2 of another alternative embodiment of a UTDDA having an open end and adhesive ring thereon.

The UTDDA 100C is a hollow cylindrically shaped object, of construction similar to that described above with respect to FIG. 2. Between the outer applicator wall 802 and the inner applicator wall 201 is a wick 850, made of material such as high-absorbency polypropylene. Both the inner and outer applicator walls 801 and 802 are basically cylindrical and axially aligned, with the exception of two locations on the inner applicator wall 801 where two grooves are cut on the inside surface of the inner applicator wall 801 for the two O-rings 820 and 830 to fit into the assembly. The location and orientation of the grooves, and the two O-rings 870 and 830 are shown in FIG. 8. As shown in FIG. 8, grooves cut into the outer diameter of the ultrasonic horn are matched to the placement of the O-rings 820 and 830 to facilitate a secure fit between the UTDDA 100B and the ultrasonic horn.

Again in reference to FIG. 8, the drug inlet septum 840 is located between the outer applicator wall 802 and the inner applicator wall 801 approximately halfway between the top and bottom of the UTDDA 100B. The septum is constructed of a silicone rubber material, designed to be impervious to liquids yet allow injection of the microparticles suspension into the UTDDA 100B using a hypodermic needle. The solution marking level 860 is pre-marked on the side of the UTDDA 100B to indicate the proper volumetric measure of microparticles suspension to be administered.

At the base of the UTDDA 100B, the porous membrane 880 is fixedly attached to the inner applicator wall 801. The membrane 880, constructed of a non-woven polypropylene or other similar hydrophobic material, resists the passage of the aqueous liquid due to its non-wettable surface and small diameter of the pores in range of 1-100 microns (μm). A removable protective film 865, which is preferably a thin plastic sheet, is removably connected to the porous membrane 880 by a ring 885 of medical adhesive which has two purposes.

The first purpose of the adhesive ring 885 is to adhere the protective film 865 to the base of the UTDDA 100B. The second purpose is to form a seal when the UTDDA 100B is applied to the patient's skin, preventing leakage of fluid into the surroundings.

The adhesive ring 885 may be composed, for example, of an acrylic adhesive, a rubber-type adhesive, or a silicone adhesive as described above with respect to adhesive ring 785.

In operation, the sterilized UTDDA 100C operated substantially as described above with respect to UTDDA 100B, except that there is no porous membrane (element 780 in FIG. 7) to contain the suspension. Instead the microparticles suspension is introduced therein by injection through septum 840 from a syringe through a cannula (not shown).

After the protective film 865 is peeled away as shown, the adhesive ring 885 is exposed at the bottom of UTDDA 100C so as to be placed in contact with the patient's skin and form a temporary seal thereto. Fluid which nevertheless spills out from the region of the seal is generally absorbed by the wick 850. After use, the UTDDA 100C is removed form the ultrasound tip and discarded.

Figure 9:
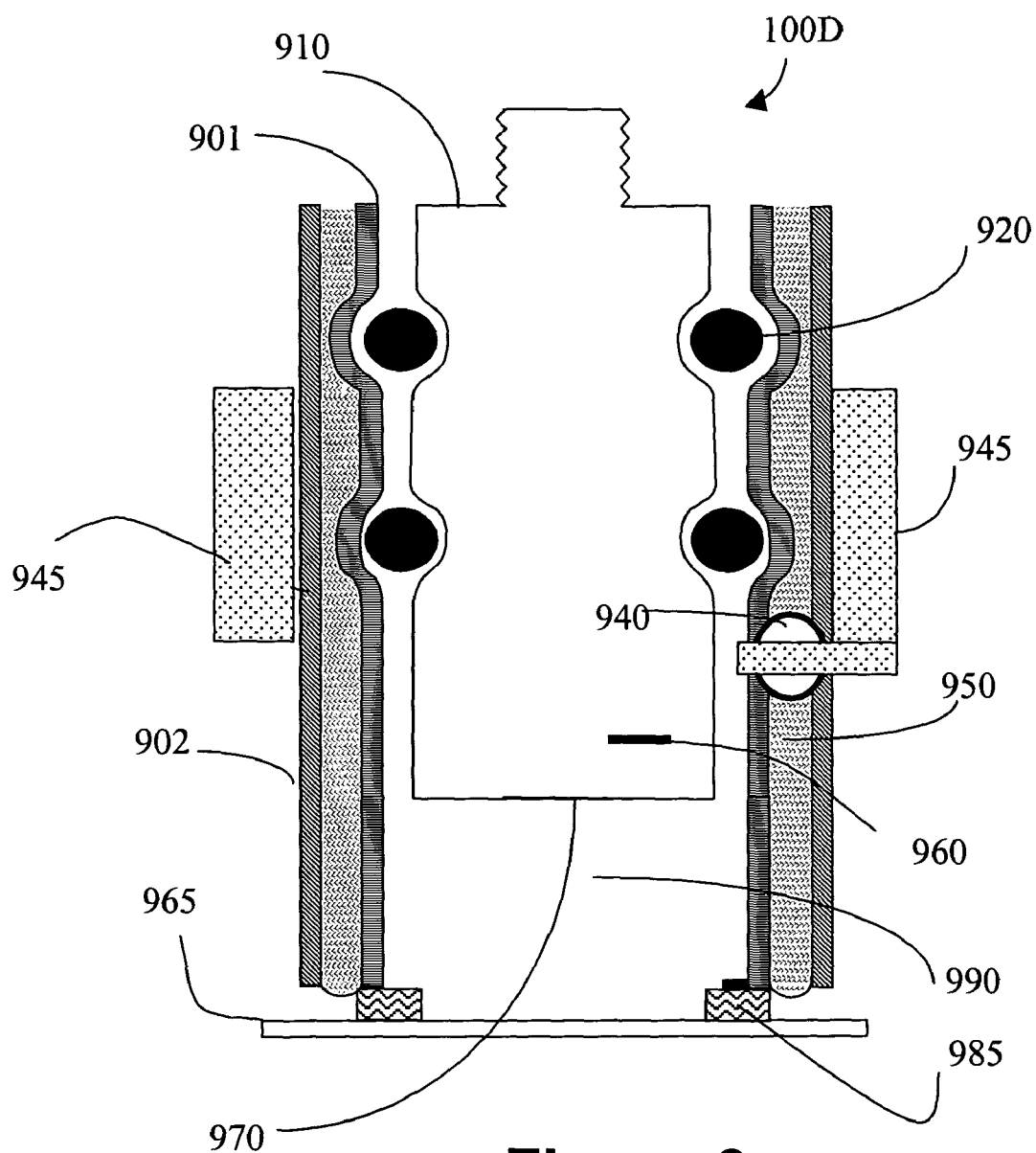
FIG. 9 is a view similar to FIG. 2 of yet another alternative embodiment of a UTDDA having a ring-shaped reservoir containing the microparticles suspension.

It is to be understood that an alternative embodiment of the UTDDA 100C (or an other version, as shown in FIGS. 7 and 9 for example) may omit the wick 850 and outer wall 802, especially if it is determined empirically that the adhesive ring 885 generally forms such a good seal in use that leakage onto surrounding skin is minimal.

FIG. 9 is a schematic of another example of an ultrasonic transdermal drug delivery applicator (UTDDA) 100D in accordance with the invention. It includes an inner applicator wall 901, an outer applicator wall 902, a first O-ring 920, a second O-ring 930, a wick 950, a microparticles suspension inlet septum 940, a solution level marking 960, a removable protective film 965, here shown in place, and a ring-shaped reservoir 945 containing a microparticles suspension that includes microparticles containing encapsulated drugs. The figure also shows parts of the ultrasonic horn (element 80 of FIG. 1), including a tip of ultrasonic horn 910, and a bottom of ultrasonic horn tip 970.

The UTDDA 100D is a hollow cylindrically shaped object, of construction similar to that described above with respect to FIG. 2. Between the outer applicator wall 902 and the inner applicator wall 201 is a wick 950. Both the inner and outer applicator walls 901 and 902 are basically cylindrical and axially aligned, with the exception of two locations on the inner applicator wall 901 where grooves are cut on the inside surface of the inner applicator wall 901 for the two O-rings 920 and 930 to fit into the assembly. The location and orientation of the grooves, and the two O-rings 920 and 930 are shown in FIG. 9.

Again in reference to FIG. 9, the drug inlet septum 940 is located between the outer applicator wall 902 and the inner applicator wall 901 approximately halfway between the top and bottom of the UTDDA 100D. The septum may be constructed of a silicone rubber material, designed to form a seal around a pipe extending from the reservoir 945 into the cavity 990 of UTDDA 100D. The solution marking level 960 is pre-marked on the side of the UTDDA 100D to indicate the proper volumetric measure of microparticles suspension to be administered.

At the base of the UTDDA 100D, a protective film 965, is removably connected to the UTDDA by a ring 985 of medical adhesive, which functions similarly to the adhesive ring 885 described above.

In operation, the sterilized UTDDA 100D operated substantially as described above with respect to UTDDA 100C, except that the microparticles suspension is provided from the reservoir 945 through a pipe extending through septum 940 rather than by a syringe and needle. After the protective film 965 is peeled away, the adhesive ring 985 is exposed at the bottom of UTDDA 100D so as to be placed in contact with the patient's skin and form a temporary seal thereto. Any fluid which nevertheless spills out from the region of the seal is absorbed by the wick 950. After use, the UTDDA 100D is removed form the ultrasound tip and discarded.

EXAMPLE

In the Franz Cell apparatus shown in FIG. 5, a 2% microparticles suspension in saline was placed in the donor compartment over the heat-split human cadaver epidermis. The receiver compartment was filled with the saline solution. Ultrasound horn was submerged in microparticles suspension at 6 mm height above the skin surface. Ultrasound of 20 kHz and intensity of 19 W cm.sup.-2 was turned on for periods of 15 sec and off for 59.9 sec. The total exposure time to ultrasound was 90 sec. The AC current of 1 V and 10 Hz was measured during the ultrasound exposure time (not shown) to determine skin permeability in presence of different size microparticles. The following microparticle sizes were investigated: 1.5 μm, 5.2 μm, 11.9 μm, 25 μm, 40 μm and 173 μm. The 2% suspensions in saline solution with microparticles of the following sizes 1.5 μm, 5.2 μm, 11.9 μm, and 173 μm. were obtained from Seradyn Mitsubishi Kasei Corp., 1200 Madison Ave., Indianapolis, Ind. 46225. Particles of other two sizes 25 μm and 40 μm were obtained from Aldrich). The effect of the microparticle size on the transdermal flux and skin conductivity is shown in Table 1.

TABLE 1

| ULTRASOUND EXPOSURE TIME (sec) | WITHOUT MICRO-PARTICLES | CONDUCTANCE ACROSS THE SKIN ($10^{-6}/\Omega$) | | | | | |
|---|---|---|---|---|---|---|---|
| | | 1.51 μm | 5.2 μm | 11.9 μm | 25 μm | 40 μm | 173 μm |
| 0 | 36 | 23 | 37 | 34 | Not measured | 24 | 40 |
| 15 | 53 | 40 | 45 | 50 | Not measured | 28 | 52 |
| 30 | 55 | 50 | 50 | 60 | Not measured | 35 | 60 |
| 45 | 67 | 90 | 70 | 83 | Not measured | 36 | 61 |
| 60 | 76 | 128 | 85 | 120 | Not measured | 46 | 61 |
| 75 | 124 | 140 | 110 | 225 | Not measured | 50 | 62 |
| 90 | 151 | 165 | 180 | 290 | Not measured | 51 | 65 |
| TOTAL PENETRATION OF SKIN BY MICRO-PARTICLES | N/A | YES | YES | YES | YES | NO | NO |

It is apparent from Table 1 that microparticles of up to 25 μm penetrated into the skin under the conditions tested, whereas particles larger than about 40 μm did not penetrate. In general, suspensions consisting essentially of microparticles of diameters less than 40 μm are preferred for use with the present invention, although if the conditions are varied to produce relatively large micropores in the skin, somewhat larger microparticles would also be effective and could be used if desired. Desirably the average diameter of microparticles useful in the invention are from 1 μm to 35 μm in diameter, and commonly could be from 5 μm to 25 μm.

The many features and advantages of the present invention are apparent from the detailed specification, and thus, it is intended by the appended claims to cover all such features and advantages of the described method and apparatus that follow the true spirit and scope of the invention. Furthermore, since numerous modifications and changes will readily occur to those of skill in the art, it is not desired to limit the invention to the exact construction and operation described herein. Moreover, the method and apparatus of the present invention, like related apparatus and methods used in medical applications tend to be complex in nature and are often best practiced by empirically determining the appropriate values of the operating parameters or by conducting computer simulations to arrive at a best design for a given application. Accordingly, other embodiments are within the scope of the following claims.

The invention claimed is:

1. A method for sonoporation for intradermal delivery of a microparticles suspension containing a beneficial substance to be released into an area of a patient's skin comprising; (a) providing a container having a first end and a second end, said second end having thereon a ring of skin-removable resilient medical adhesive material and being covered by a removable protective film; (b) submerging the tip of an ultrasound horn in said microparticles suspension through said first end of the container; (c) removing the protective film; and (d) placing said second end in contact with an area of a patient's skin intended to receive said beneficial substance and (e) applying ultrasound radiation to said microparticles suspension at a frequency, an intensity, for a period of time, and at a distance from the skin, effective to generate cavitation bubbles, wherein said cavitation bubbles collapse and transfer their energy into the skin area thus causing the formation of pores in the skin area; and wherein said ultrasound radiation intensity and distance from the skin area are also effective in generating ultrasonic jets, said ultrasonic jets driving said microparticles through said formed pores into the skin area with a majority of the microparticles remaining intact.

2. The method of claim 1 wherein substantially all of said microparticles remain intact upon being driven into the skin area.

3. The method of claim 1, wherein said second end has a microporous membrane thereover.

4. The method of claim 1, wherein the average diameter of the microparticles is from 0.1 micron to 50 microns.

5. The method of claim 4, wherein the average diameter of the microparticles is from 1 micron to 5 microns.

6. The method of claim 1, wherein the frequency of said ultrasound radiation is from 1 kHz to 30 kHz.

7. The method of claim 6, wherein the frequency of said ultrasound radiation is about 20 kHz.

8. The method of claim 1, wherein the microparticles are liposomes, biodegradable spherical particles made of polymeric shell with a drug inside, or polymeric spheres with the drug attached to the surface of the microparticles.

9. The method of claim 1, wherein the container has therewithin a capsule containing a predetermined quantity of microparticles suspension, further comprising the step of releasing said microparticles suspension from said capsule after the aforesaid step (c).

10. The method of claim 1, wherein said container is removed from the ultrasound horn and disposed of after a single use.

11. The method of claim 1, wherein said container comprises: (1) an outer wall; (2) an inner wall; and (3) an absorbent wick placed between said inner and outer wall, said wick absorbing any excess microparticles suspension; and wherein said ring of medical adhesive is on the end of the inner wall, said adhesive ring being constructed to prevent microparticles suspension from leaking out during ultrasonic application.

12. The method of claim 11, wherein said medical adhesive is a silicone, rubber or acrylic.

13. The method of claim 11, wherein said container further comprises an inlet septum for filling said container with the microparticles suspension.

14. The method of claim 11, wherein said container further comprises a hollow ring extending thereabout, said hollow ring containing microparticles suspension, and further comprising the step of introducing into microparticles suspension into said container from said hollow ring after the aforesaid step (3).

15. The method of claim 1 wherein said tip comprises a flat distal end surface.

16. The method of claim 1 wherein said tip comprises a concave distal end surface.

17. The method of claim 1 wherein said tip comprises a flat distal end surface having a plurality of depressions.

18. The method of claim 1, wherein said tip comprises a body having a marking indicating a level of the microparticles suspension to be contained in the container.

19. A method for sonoporation for intradermal delivery of a microparticles suspension containing a beneficial substance to be released into an area of a patient's skin comprising: (a) providing a container having a first end and a second end, said second end being covered by a porous membrane removably covered by a protective film; (b) submerging the tip of an ultrasound horn in said microparticles suspension through said first end of the container; (c) placing said second end in contact with an area of a patient's skin intended to receive said beneficial substance and (d) applying ultrasound radiation to said microparticles suspension at a frequency, an intensity, for a period of time, and at a distance from the skin, effective to generate cavitation bubbles, wherein said cavitation bubbles collapse and transfer their energy into the skin area thus causing the formation of pores in the skin area; and wherein said ultrasound radiation intensity and distance from the skin area are also effective in generating ultrasonic jets, said ultrasonic jets driving said microparticles through said formed pores into the skin area with a majority of the microparticles remaining intact.

20. The method of claim 19, wherein substantially all of said microparticles remain intact upon being driven into the skin area.

21. The method of claim 19, wherein the average diameter of the microparticles is from 0.1 micron to 50 microns.

22. The method of claim 21, wherein the average diameter of the microparticles is from 1 micron to 5 microns.

23. The method of claim 19, wherein the frequency of said ultrasound radiation is from 1 kHz to 30 kHz.

24. The method of claim 23, wherein the frequency of said ultrasound radiation is about 20 kHz.

25. The method of claim 19, wherein said second end has thereon a ring of skin-removable resilient medical adhesive material which is covered by said removable protective film.

* * * * *